United States Patent
Rodfalk et al.

(10) Patent No.: US 9,063,110 B2
(45) Date of Patent: Jun. 23, 2015

(54) MEASUREMENTS IN METALLURGICAL VESSELS

(75) Inventors: Albert Rodfalk, Dalby (SE); Jan-Peter Nilsson, Lund (SE); Patrik Bloemer, Halmstad (SE); Anthony Lyons, Swallownest Sheffield (GB)

(73) Assignee: AGELLIS GROUP AB, Lund (SE)

( * ) Notice: Subject to any disclaimer, the term of this patent is extended or adjusted under 35 U.S.C. 154(b) by 4 days.

(21) Appl. No.: 13/695,331

(22) PCT Filed: Apr. 27, 2011

(86) PCT No.: PCT/SE2011/050512
§ 371 (c)(1),
(2), (4) Date: Oct. 30, 2012

(87) PCT Pub. No.: WO2011/136729
PCT Pub. Date: Nov. 3, 2011

(65) Prior Publication Data
US 2013/0038337 A1 Feb. 14, 2013

Related U.S. Application Data

(60) Provisional application No. 61/282,975, filed on May 3, 2010.

(30) Foreign Application Priority Data

Apr. 30, 2010 (SE) ........................................ 1000437

(51) Int. Cl.
*G01R 27/04* (2006.01)
*G01R 27/32* (2006.01)
(Continued)

(52) U.S. Cl.
CPC .............. *G01N 33/206* (2013.01); *B22D 2/003* (2013.01); *F27D 21/00* (2013.01); *G01F 23/24* (2013.01); *G01F 23/245* (2013.01); *G01F 23/26* (2013.01); *G01N 27/06* (2013.01)

(58) Field of Classification Search
CPC ........ A61B 5/05; A61B 5/076; A61B 5/0031; A61B 2560/0219; A61B 2560/0233; G01N 22/00; G01R 27/04; G01R 27/16; G01R 27/32; G01B 7/30; G01B 7/003; G01B 7/107

USPC .............................. 324/633, 207.16, 230, 629
See application file for complete search history.

(56) References Cited

U.S. PATENT DOCUMENTS 3,395,908 A * 8/1968 Woodcock ........................ 266/99
3,663,204 A * 5/1972 Jungwirth ........................ 75/375
(Continued)

FOREIGN PATENT DOCUMENTS

CN 1475799 A 2/2004
DE 3201799 8/1983
(Continued)

OTHER PUBLICATIONS

International Search Report for PCT/SE2011/050512, Completed by the Swedish Patent Office on Jul. 22, 2011, 4 Pages.
(Continued)

*Primary Examiner* — Tung X Nguyen
*Assistant Examiner* — Giovanni Astacio-Oquendo
(74) *Attorney, Agent, or Firm* — Brooks Kushman P.C.

(57) ABSTRACT

A method, implemented by a software-controlled computer device and/or by dedicated hardware, for probing an electrically conductive target material, e.g. molten metal or semiconductor material, in a metallurgical vessel. In the method, a measurement signal is acquired from a sensor, which is inserted into the target material, during a relative displacement between the electrically conductive target material and the sensor, the measurement signal being indicative of electrical conductivity in the vicinity of the sensor. The measurement signal is generated to represent momentary changes in an electromagnetic field around the sensor, which is created by operating at least one coil in the sensor. Based on the measurement signal, a signal profile is generated to be indicative of the electrical conductivity as a function of the relative movement. The method enables a probing of the internal distribution of the target material in the vessel at any level of detail.

22 Claims, 7 Drawing Sheets

(51) Int. Cl.
| | |
|---|---|
| *G01N 33/20* | (2006.01) |
| *B22D 2/00* | (2006.01) |
| *F27D 21/00* | (2006.01) |
| *G01F 23/24* | (2006.01) |
| *G01F 23/26* | (2006.01) |
| *G01N 27/06* | (2006.01) |

(56) References Cited

U.S. PATENT DOCUMENTS

| | | | | |
|---|---|---|---|---|
| 4,150,974 | A | | 4/1979 | Kemlo |
| 4,413,810 | A | * | 11/1983 | Tenberg et al. ............... 266/94 |
| 4,635,832 | A | * | 1/1987 | Angerer et al. ............. 222/590 |
| 4,647,854 | A | | 3/1987 | Yamada et al. |
| 4,708,191 | A | * | 11/1987 | Block et al. ............... 164/151.3 |
| 4,841,770 | A | | 6/1989 | Davies |
| 4,880,212 | A | | 11/1989 | Hagglund et al. |
| 5,048,594 | A | * | 9/1991 | Cecchini et al. ............ 164/453 |
| 5,198,749 | A | | 3/1993 | Guthrie et al. |
| 5,241,262 | A | * | 8/1993 | Guthrie et al. ............. 324/71.1 |
| 5,372,355 | A | * | 12/1994 | Henn et al. .................. 266/236 |
| 5,435,196 | A | * | 7/1995 | Cassidy ....................... 73/863.11 |
| 5,781,008 | A | * | 7/1998 | Muller et al. ................ 324/230 |
| 5,827,474 | A | | 10/1998 | Usher et al. |
| 6,139,180 | A | * | 10/2000 | Usher et al. .................... 374/1 |
| 6,911,818 | B2 | | 6/2005 | Julius |
| 8,661,891 | B2 | * | 3/2014 | Xie et al. ...................... 73/295 |
| 2007/0173117 | A1 | | 7/2007 | Dams et al. |
| 2007/0176334 | A1 | | 8/2007 | Knevels et al. |
| 2009/0073207 | A1 | * | 3/2009 | Takeuchi ....................... 347/11 |

FOREIGN PATENT DOCUMENTS

| | | |
|---|---|---|
| GB | 2183849 | 6/1987 |
| JP | 58063818 | 4/1983 |
| JP | 58144716 | 8/1983 |
| JP | 62044629 | 2/1987 |
| JP | 1094201 | 4/1989 |
| JP | 04348230 | 12/1992 |
| JP | 11104797 | 4/1994 |
| JP | 06258129 | 9/1994 |
| JP | 10122544 | 5/1998 |
| JP | 2003049215 | 2/2003 |
| JP | 2006255756 A | 9/2006 |
| WO | 2009109931 | 9/2009 |

OTHER PUBLICATIONS

Korp et al. IEEE ISIE Jun. 20-23, 2005, p. 1099-1104, "On Conductivity Measurements at Temperatures Exceeding 1500 Degrees Celsius."
Japanese Office Action Issued Mar. 10, 2015, 5 pgs.
Search Report from Chile Patent Office issued Oct. 3, 2014, 1 pg.

* cited by examiner

MEASUREMENTS IN METALLURGICAL VESSELS

CROSS-REFERENCE TO RELATED APPLICATIONS

The present application claims the benefit of Swedish patent application No. 1000437-2, filed on Apr. 30, 2010, and U.S. provisional application No. 61/282,975, filed on May 3, 2010, both of which are incorporated herein by reference.

FIELD OF TECHNOLOGY

The invention relates to procedures in metallurgical vessels such as furnaces, smelters and other refining or holding vessels for processing of electrically conducting materials such as metals and semiconductors.

BACKGROUND

For many years, it has been possible to locate the slag surface in a metallurgical vessel, if it is stable, by using microwave, laser, eddy-current, radioactive, camera or float technology. It has also been possible to roughly measure the extent of different zones in the vessel by employing the use of a simple dip pin/sounding bar technology where a metal rod attached to a chain or other delivery system is first immersed in the molten material and then withdrawn for visual inspection. An experienced operator may thereby visually estimate the location of a particular zone in the vessel at that moment in time.

There are also electronic measurements devices designed for measuring the thickness or other properties of the slag layer. U.S. Pat. No. 5,781,008 discloses a measurement device which uses a combination of sensors attached to a moveable lance. One sensor is arranged at the tip of the lance to sense contact with the slag layer and another sensor is configured to remotely (via eddy current) sense the distance to the interface between the slag layer and the molten metal. As the tip contacts the slag layer, the eddy current sensor is operated to determine the distance to the slag/melt interface. Since the distance between the sensors is known, the slag layer thickness can be determined.

U.S. Pat. No. 4,647,854 and JP06-258129 suggest the use of an eddy current-type distance measuring sensor suspended above the slag layer in a metallurgical vessel for detecting the level of molten metal in the vessel. The sensor comprises an excitation coil for generating an oscillating electromagnetic field and one or more eddy current detecting coils.

U.S. Pat. No. 4,841,770, US2007176334A1, JP2003049215 and U.S. Pat. No. 4,880,212 all disclose different moveable lances with measurement devices (probes) configured to be immersed into the slag layer so as to generate a signal indicative of the slag thickness. The sensors and sensor electronics are designed to sense the interface between the slag layer and molten metal, e.g. using electrode pairs, or inductive coils connected to oscillators. Thus, the sensors and the sensor electronics are designed to provide a well-defined switch point at the interface between the slag layer and the molten metal.

DE3201799 discloses use of electrodes for measuring the conductivity of a slag layer.

JP1094201 describes a technique for measuring the thickness of molten slag, by arranging a magnetic field generation coil and a pair of detection coils above the slag, and by driving the coils such that a resistance component indicative of the thickness may be isolated by an impedance measuring device.

US2007/173117 discloses a design of a measuring head for attachment to a lance, the measuring head including a temperature sensor and an oxygen sensor for measuring a corresponding parameter of the slag layer or the molten metal beneath the slag layer.

U.S. Pat. No. 5,198,749 discloses an sample probe operable to suck molten metal through an orifice for measuring the number and size of non-conductive inclusion particles.

U.S. Pat. No. 5,827,474 discloses a technique for measuring the depth of molten steel and slag in a metallurgical vessel. A probe of electrically conductive material has a proximal end electrically connected to a voltmeter, and a distal end movable between the vessel floor and the air-slag interface or the slag-steel interface in the vessel. The distal end thus acts as an electrode, and the depth of molten steel or the depth of the slag is determined by comparing the differences in electrical potential detected by the voltmeter while noting the vertical position of the distal end of the probe.

JP11104797 discloses a technique for avoiding outflow of molten slag from a ladle during tapping of molten metal into a tundish. The technique involves comparing the electrical conductivities measured by a pair of electrodes in a bottom part of the ladle and by a pair of electrodes in the tundish. A deviation in measured conductivity between the ladle and the tundish is taken as an indication that the molten slag has reached the electrodes in the ladle.

U.S. Pat. No. 4,150,974 discloses a technique for positioning the snorkel of a vacuum degassing apparatus beneath the interface of the molten metal and the slag in a ladle. The location of the interface is determined by vertically displacing an electrode which is in electrical contact with the material in the ladle. The position of the metal-slag interface is determined by noting a change in the voltage produced by the electrode.

WO2009/109931 discloses a probe for use in control of a solvent exchange process. Along its extent, the probe carries a series of pairs of sensing pins for measuring resistance. By immersing the probe into the material subjected to the exchange process, a resistivity profile along the length of the probe may be determined.

In some melting/refining processes, the vessel contains a number of material layers, as well as areas of gradual change or material mixing. For example, in processes for melting copper or platinum, it is known that there is a large mixing zone between the slag layer and the matte. At present, there is no versatile technique for probing of any part of the target material in a metallurgical vessel, e.g. for the purpose of analysing the presence and/or location of different zones/layers, such as material layers and mixing zones located beneath a slag layer in the vessel. Such a technique would have great value, e.g. to decision making and process optimization.

To the extent that the techniques proposed in aforesaid U.S. Pat. No. 5,827,474, JP11104797, U.S. Pat. No. 4,150,974 and WO2009/109931 may be applied for such use, these techniques all rely on probes with electrodes/sensing pins that must be in direct galvanic contact with the target material in the metallurgical vessel. Such probes will have an elevated sensitivity to deposits and contaminations, as well as a potentially reduced life since the electrodes/sensing pins are directly exposed to the harsh environments in the vessel.

SUMMARY

It is an object of the invention to at least partly overcome one or more of the above-identified limitations of the prior art.

These and other objects, which may appear from the description below, are at least partly achieved by means of a method for enabling zone identification, a computer program product, a computer-readable medium, devices for enabling zone identification, and a processing plant according to the independent claims, embodiments thereof being defined by the dependent claims.

A first aspect of the invention is a method of probing an electrically conductive target material in a metallurgical vessel. The method comprises the steps of: acquiring a measurement signal from a sensor, which is inserted into the target material, during a relative displacement between the electrically conductive target material and the sensor, the measurement signal being indicative of electrical conductivity in the vicinity of the sensor; and generating, based on the measurement signal, a signal profile indicative of the electrical conductivity as a function of the relative movement. The method further comprises the steps of operating at least one coil in the sensor to generate an electromagnetic field around the sensor, and generating the measurement signal to represent momentary changes in the electromagnetic field.

The method is versatile to the extent that it enables probing of the internal distribution of the target material in the vessel at any level of detail, via the signal profile which contains a number measurement values for different relative positions between the target material and the sensor, where the level of detail may be adjusted by adjusting the number of measurement values. The method thus has the ability to provide information about zones/layers that differ by e.g. composition of matter, degree of melting, degree of mixing, or any combinations thereof. For example, the signal profile may be generated to be indicative of the electrical conductivity in the target material beneath a top material layer, which may be a slag layer. For example, the generated signal profile may enable probing beneath a slag layer, e.g. to detect the presence of one or more zones and/or to determine the location/extent of such zone(s).

By generating the measurement signal to represent momentary changes in an electromagnetic field around the sensor, which is created by operating at least one coil in the sensor, there is no need for direct galvanic contact between the sensor and the target material. The coil(s) may thus be enclosed in a casing that protects the coil(s) and any associated electronic components from the harsh environments inside the vessel. Any deposits and contaminations on the surface of the casing will have little or at least limited impact on the accuracy of the resulting signal profile. It is also possible, for avoiding that molten material or slag adheres to the surface of the casing, to arrange one or more protective sleeves around the casing, the sleeves being designed to be consumed during the measurement. The protective sleeves may e.g. be made of cardboard, which will gradually burn off during the measurement, thereby automatically removing deposits from the surface of the casing.

In certain embodiments, the signal profile is indicative of the electrical conductivity in the target material beneath a top material layer, whereby the signal profile enables identification of one or more zones in the target material beneath the top material layer.

In certain embodiments, the signal profile is generated to be indicate of a relative change in the electrical conductivity as a function of the relative movement.

In certain embodiments, the target material is a molten material at a temperature in the range of 600-2000° C.

In certain embodiments, the target material comprises at least two zones which differ by at least one of: a composition of matter, a degree of melting, and degree of mixing.

A second aspect of the invention is a computer-readable medium comprising program instructions that, when executed by a processor, performs the method of the first aspect.

A third aspect of the invention is a computer program product loadable into a memory of a computing device for performing the method of the first aspect.

A fourth aspect of the invention is a device for probing an electrically conductive target material in a metallurgical vessel. The device comprises means for acquiring a measurement signal from a sensor, which is inserted into the target material, during a relative displacement between the electrically conductive target material and the sensor, the measurement signal being indicative of electrical conductivity in the vicinity of the sensor; means for generating, based on the measurement signal, a signal profile indicative of the electrical conductivity as a function of the relative movement. The device further comprises means for operating at least one coil in the sensor to generate an electromagnetic field around the sensor, and means for generating the measurement signal to represent momentary changes in the electromagnetic field.

A fifth aspect of the invention is a device for probing an electrically conductive target material in a metallurgical vessel. The device comprises: a controller configured to acquire a measurement signal from a sensor, which is inserted into the target material, during a relative displacement between the electrically conductive target material and the sensor, the measurement signal being indicative of electrical conductivity in the vicinity of the sensor; and a signal processor configured to generate, based on the measurement signal, a signal profile indicative of the electrical conductivity as a function of the relative movement. The controller is further configured to operate at least one coil in the sensor to generate an electromagnetic field around the sensor, and to generate the measurement signal to represent momentary changes in the electromagnetic field.

A sixth aspect is a plant for processing of an electrically conductive target material, comprising: a metallurgical vessel configured to contain the target material; a lance; a sensor attached to the lance and configured to sense electrical conductivity; a drive mechanism mechanically connected to the lance and configured to move the lance with respect to the target material; and the device according to the fourth or fifth aspect.

Any one of the embodiments of the first aspect may be combined with the second to sixth aspects.

Still other objectives, features, aspects and advantages of the present invention will appear from the following detailed description, from the attached claims as well as from the drawings.

BRIEF DESCRIPTION OF THE DRAWINGS

Embodiments of the invention will now be described hereinbelow by way of example only, with reference to the accompanying schematic drawings.

DETAILED DESCRIPTION OF EXEMPLARY EMBODIMENTS

Figure 1A:
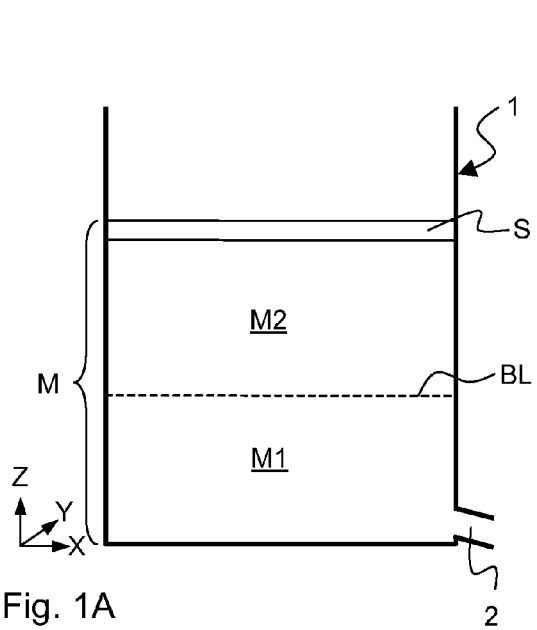
FIGS. 1A-1C are sectional views of a metallurgical vessel and different measurement scenarios.

FIG. 1A depicts a metallurgical vessel 1 that is used for processing of electrically conductive materials, such as metals or semiconductor materials. The metallurgical vessel 1 may thus be a furnace, a smelter, or any other refining or holding vessel which is designed and used for extracting a metal from its ore or from some other raw material such as scrap, for producing an alloy of different metals, for purifying a metal or an alloy, for creating any useful object from a metal or alloy, or which is designed and used for corresponding processing of semiconductor materials. Typically, the interior of the metallurgical vessel 1 is heated to temperatures of about 600-2000° C., or even higher, during such processing.

In the following, example embodiments are described in relation to a smelter used in extraction of copper. However, it is to be understood that the invention is in no way limited to this application. Throughout the description, the same reference numerals are used to identify corresponding elements.

Copper may be produced from a copper-bearing ore, e.g. CuFeS2, typically after enrichment in a flotation process. In one of many available processes for copper extraction, the enriched ore is processed in a smelter in the presence of air, limestone and sand. Here, the oxygen in the air selectively reacts with the iron to form iron oxide, FeO, and leaves copper in the form of the sulfide, CuS. The silicon dioxide in the sand reacts with the limestone and the iron oxide to form slag, $FeSiO_3$ and $CaSiO_3$. At the same time the excess sulfur in the ore reduces copper (II) sulfide, CuS, to copper (I) sulfide, $Cu_2S$, which melts and is tapped at the bottom of the smelter. The slag is less dense and floats on the top.

The molten copper (I) sulfide, called copper matte, is run into a converter furnace, where air containing oxygen is blown through the copper matte to oxidize the sulfide ions to sulfur dioxide. At the same time some of the sulfide ions reduce the copper (I) ions to impure blister copper metal. A final heating in an anode furnace is used to burn off the remaining oxygen from the blister copper metal.

The vessel 1 in FIG. 1A may be seen to depict the smelter used for processing the enriched ore, and having a tapping spout 2 for tapping the copper matte from the vessel 1. During processing, a slag layer S is formed on top of the molten material. It is known that the copper matte is formed in a matte layer (zone) M1 at the bottom of the vessel 1, and that there is a mixing or transition zone M2 between matte layer M1 and the slag layer S. The mixing zone M2 has a varying and lower content of copper than the matte layer M1. For reasons of enabling improved process control, e.g. to control the tapping, or to otherwise control or optimize the copper extraction process, it is desirable to identify the extent the mixing zone M2, the location of the border BL between the mixing zone M2 and the matte layer M1, or to quantify the amount of copper matte in the vessel.

Figure 1B:
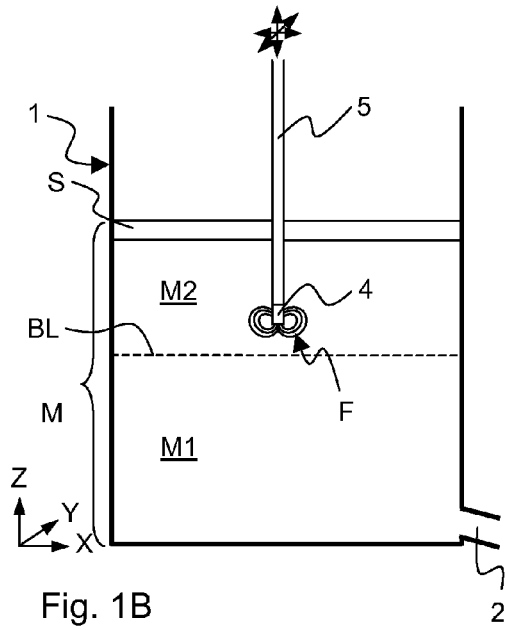

In FIG. 1B, a sensor unit 4 is mounted on a holding rod or lance 5 which is controlled for displacement in at least the vertical direction (z). As indicated, the lance 5 may also be displaceable in the horizontal directions (xy plane). The sensor unit 4 is configured to sense the electrical conductivity of the locally surrounding material. Although not shown in FIG. 1B, the sensor unit 4 is included in a measurement system which generates a signal profile that represents the distribution of conductivity within the material M that is being processed in the vessel 1 (also denoted "target material" herein). This signal profile is also denoted "conductivity profile" in the following.

As indicated by the field lines F in FIG. 1B, the sensor unit 4 may operate by generating an oscillating or time-varying electromagnetic field which extends into the surrounding material. The structure and operation of a measurement system including such a sensor unit will be described in detail further below.

The conductivity profile may be used for identifying zones M1, M2 within the molten material beneath the slag layer S. Bearing in mind the elevated temperature of the molten material, the sensor unit 4 can normally only be immersed in the molten material for a short time, typically in the order of 30-90 seconds. To protect the sensor unit 4, the front end portion of the lance 5 may be surrounded by one or more protective sleeves (not shown), e.g. made of cardboard and/or ceramic material.

The generation of the conductivity profile starts by the sensor unit 4 being lowered from a suspended position to penetrate the slag layer S and enter the molten material. The lance 5 is then moved within the molten material, while a plurality of measurement values are being obtained by means of the sensor unit 4. The lance and sensor unit combination 4, 5 is then withdrawn from the molten material. The measurement values are processed to form the conductivity profile, which thus indicates the distribution of electrical conductivity in the vessel ("spatial conductivity profile"). Such a distribution may in turn be used for identifying the location of the mixing zone M2 and the matte layer M1, respectively.

It is to be noted that the conductivity profile may be generated to indicate only relative changes in the conductivity within the molten material. It is also to be understood that the conductivity profile may contain more or less qualitative data, i.e. data affected by error sources such as unknown temperature variations, measurement errors, etc. Nevertheless, the quality of the data is sufficient to identify different zones M1, M2 and boundaries BL within the molten material. If the measurement system is configured to obtain a reference value of the conductivity (see below), the conductivity profile may be generated to represent absolute conductivity in the molten material.

Figure 2:
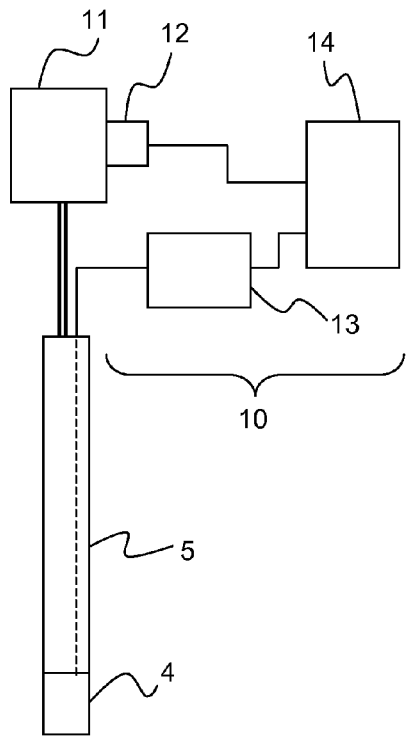
FIG. 2 is a block diagram of a measurement system associated to a lance drive mechanism.

FIG. 2 is a block diagram of a measurement system 10 used for obtaining the conductivity profile in the embodiment of FIG. 1B. A displacement unit 11 is mechanically connected to and configured to control the displacement of the lance/sensor unit 5, 4. The measurement system 10 includes a position-sensing unit 12, which is arranged to generate a position signal that indicates the momentary (absolute or relative) position of the lance 5 (or the sensor unit 4). A measurement controller 13 is connected to process an electrical signal generated by the sensor unit 4 and to output a measurement signal directly or indirectly representative of electrical conductivity.

A processing unit 14 is connected to receive and process the position signal and the measurement signal for generation of the conductivity profile.

Figure 1C:
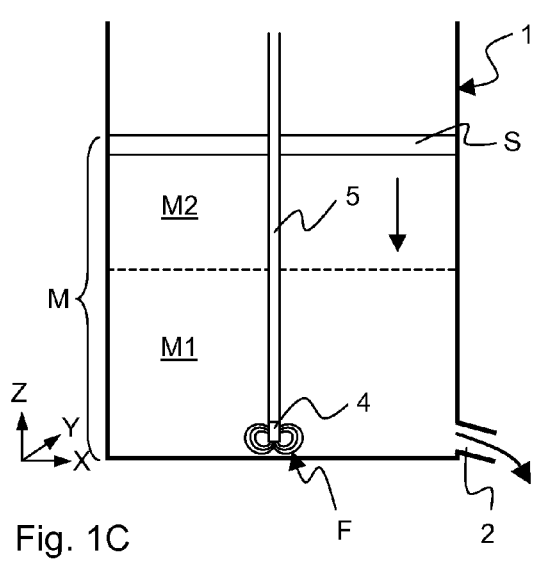

FIG. 1C illustrates another scenario for generating a conductivity profile in a metallurgical vessel 1. Like in FIG. 1B, the sensor unit 4 is displaced to penetrate the slag layer S. However, the sensor unit 4 is moved directly to a position within the vessel 1 where it then remains fixed. A plurality of measurement values are obtained by means of the sensor unit 4 in this position, while molten material is tapped from the vessel 1 at a location beneath the sensor unit 4, in this case from the spout 2 at the bottom of the vessel 1. The tapping of molten material generates a relative movement between the sensor unit 4 and the molten material. Thus, the measurement values obtained during the tapping procedure may be processed for generation of a conductivity profile that may be used to identify the location of zones M1, M2 within the molten material. Here, the conductivity profile is typically given as a function of time ("temporal conductivity profile"), since time is representative of the movement of the sensor unit 4 in relation to the molten material. It should be realized that the measurement system 10 in FIG. 2 may be used to obtain the conductivity profile in the measurement scenario of FIG. 1C.

Combinations of the scenarios in FIGS. 1B and 1C are also conceivable. For example, a spatial conductivity profile may be generated to identify one or more zones M1, M2 in the vessel 1, and then the sensor unit 4 may be positioned in relation to these zones M1, M2 for generating of a temporal conductivity profile during a tapping procedure.

Figure 3:
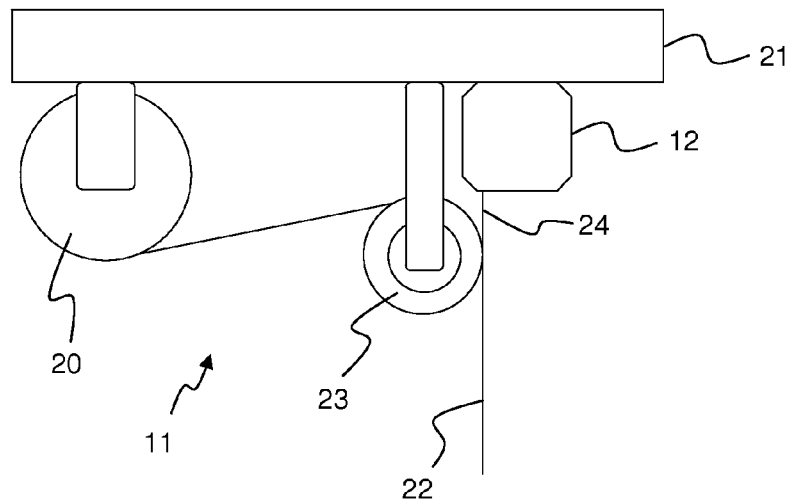
FIG. 3 is a side view of a lance drive mechanism.

Likewise, any type of displacement unit 11 may be used to impart the desired movement to the lance/sensor unit 5, 4. FIG. 3 illustrates an example of a displacement unit 11 which is configured to move the lance 5 in the vertical direction (z direction). The displacement unit 11 comprises a motor-driven winch 20 which is attached to a fixed beam 21 and operable to wind and unwind a wire cable (or chain) 22 connected to the lance. The wire cable 22 is supported by a pulley 23, which fixes the position of the lance in the horizontal direction (xy plane). Although the illustrated displacement unit 11 is configured to limit the movement of the lance to the vertical direction, it is realized that movement in the horizontal directions may be enabled by controlling the location of the pulley 23 or the beam 21. In the illustrated example, a position-sensing unit 12 in the form of a draw-wire sensor is attached to the lance to output a position signal that indicates the vertical position of the lance. The draw-wire sensor 12 detects and measures (quasi) linear position using a flexible cable 24 which is attached to the lance and which unreels from a spring-loaded spool (not shown) while the lance is lowered in the vertical direction. The position of the lance may be given in any coordinate system. It is conceivable that the position-sensing unit 12 is pre-calibrated to indicate the position of the sensor unit in a coordinate system of the vessel, e.g. in position units measured from the bottom of the vessel (cf. xyz in FIG. 1). Generally, however, the position signal indicates the position of the lance in a local coordinate system at the position-sensing unit 12, and the signal processor 14 (FIG. 2) needs to access calibration data to convert the position signal into a vessel coordinate system.

It should be understood that any suitable type of position-sensing unit 12 may be used, such as an encoder connected to the winch 20 or its drive motor or any form of remote position-sensing unit, such as a laser rangefinder. Alternatively, the position signal may be given by a control signal for the drive motor.

It is conceivable that the signal processor 14 generates the spatial conductivity profile without access to an external position signal. For example, if the lance 5 is displaced at a constant and known (pre-set) speed in the vertical direction, the measurement values may be associated with a vertical position in the vessel 1 based on a single reference position. For example, if the start or stop of the lance movement is detectable in the sequence of measurement values, the time point of each measurement value may be converted to a position in the vessel 1, based on the known displacement speed of the lance and a known start/stop location. Alternative reference positions are discussed below in relation to FIGS. 4 and 5.

Figure 4:
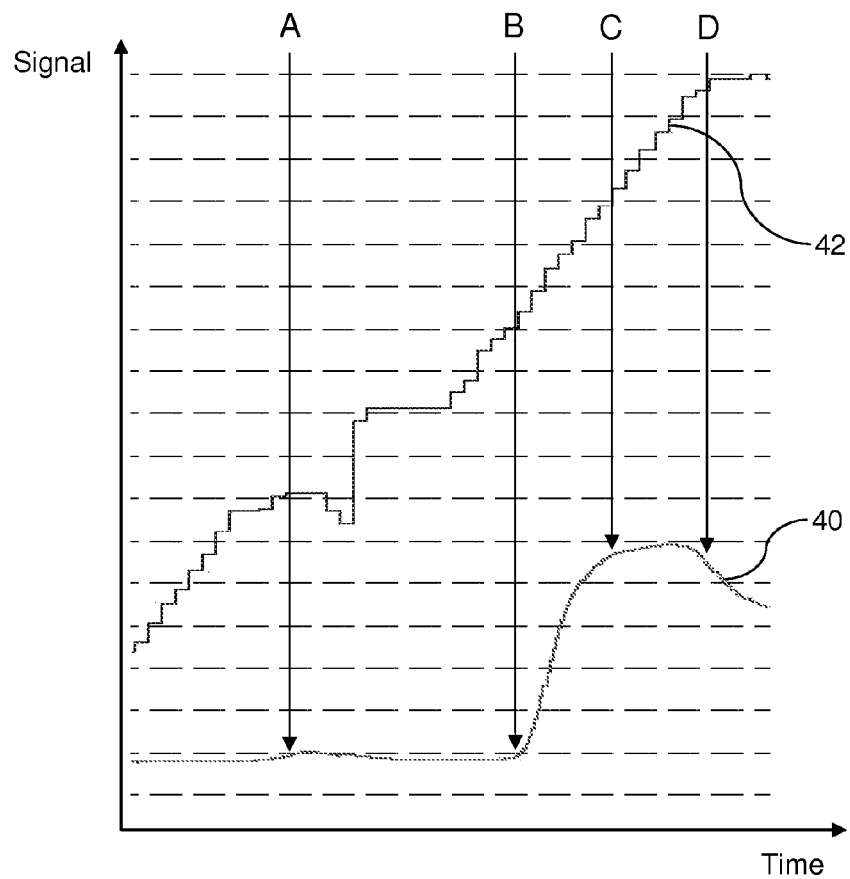
FIG. 4 is a graph of a conductivity signal and a position signal acquired by a measurement system.

FIG. 4 is a graph that illustrates a conductivity signal (measurement signal) 40 and a position signal 42 obtained in the embodiment of FIG. 1B. The conductivity signal 40 represents the relative change of electrical conductivity as a function of time, and the position signal represents the momentary position of the lance/sensor unit 5, 4 as measured by the position-sensing unit 12. In this example, the conductivity signal 40 is obtained while the lance 5 in FIG. 1B is lowered into the vessel 1 until the lance 5 is in contact with the bottom surface of the vessel 1. Then, the displacement unit 11 is reversed and the lance 5 is withdrawn in the vertical direction through the molten material and out of the vessel 1. Provided that the sensor unit 4 is intact, it is possible to obtain a corresponding conductivity signal (not shown) during the withdrawal of the lance 5. In one implementation, conductivity signals 40 obtained during lowering/immersion and hoisting/withdrawal, respectively, are matched and combined to reduce the influence of measurement noise and other measurement errors (e.g. by summing, averaging, etc) and/or to increase the spatial resolution of the conductivity profile (e.g. by combining conductivity values acquired at different positions along the path of the sensor). It is also conceivable that the lance 5 is moved along the same path for a larger number of times in order to produce a set of conductivity signals 40, one for each passage, which may be combined to provide a further improved conductivity profile.

The arrows A-D indicate different borders/interfaces that may be identified based on the conductivity signal. Arrow A indicates a small change in conductivity corresponding to the sensor unit 4 going through the top of the slag layer S. The seemingly strange disruption in the position signal 42 on entry into the slag layer S is caused by the fact that the lance 5 had to be struck manually to break through the solidified slag layer S.

Arrow B indicates that the sensor unit 4 is entering the mixing zone M2, which is evidenced by the increasing conductivity. Arrow C indicates that the sensor unit 4 is entering the matte layer M1, since the increase in conductivity essentially ceases. While the sensor unit 4 traverses the matte layer M1, the conductivity remains essentially constant until the sensor unit 4 reaches the bottom surface of the vessel 1 (arrow D). It is seen that the conductivity signal indeed is useful for identifying different zones M1, M2 and boundaries BL in the molten material.

It is understood that the spatial conductivity profile may be obtained by matching time points in the conductivity profile 40 to time points in the position signal 42.

Since the location of the top of the slag layer S is detectable in the conductivity signal 40 (arrow A), this location may be used to calibrate the conductivity signal 40 into a vessel coordinate system, without the need for a position signal 42. This presumes that the location of the top surface of slag layer S is known, e.g. determined by a supplementary measurement system, and that the lance 5 is displaced at a known and fixed speed.

Figure 5:
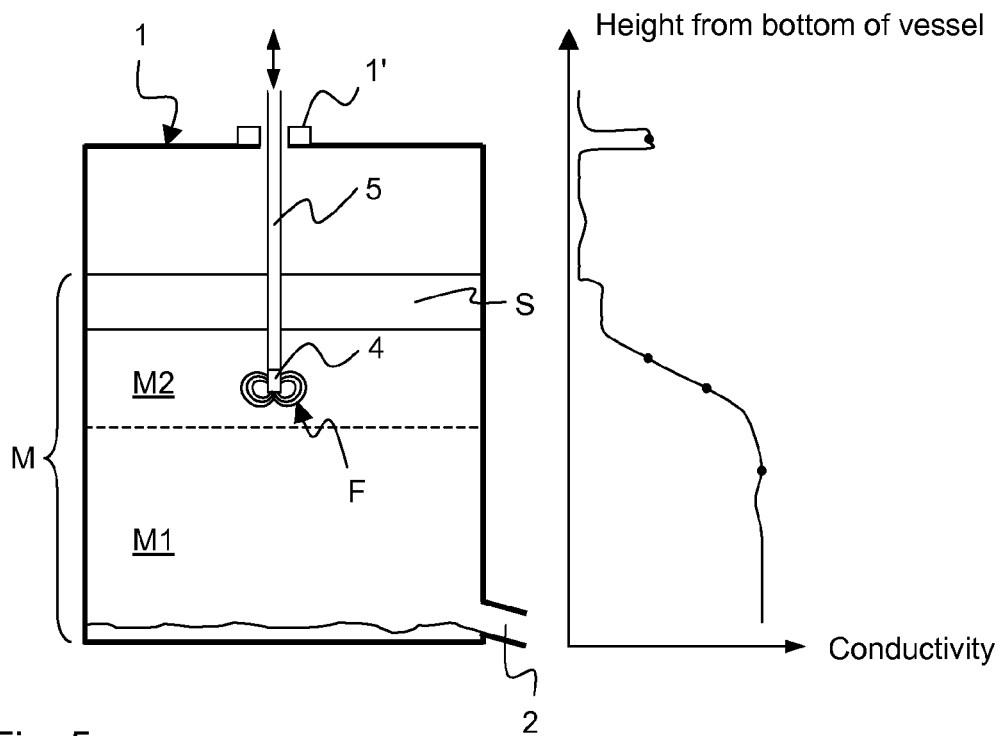
FIG. 5 is a side view of a metallurgical vessel and a conductivity profile matched to the extent of the vessel.

FIG. 5 illustrates an embodiment in which the sensor unit 4 passes a region 1' of known conductivity during the measurement session. This allows for calibration of the conductivity signal/profile into absolute conductivity. Provided that measurement system is controlled to acquire a measurement value when the sensor unit 4 passes the known conductivity, it is possible to convert all measurement values into absolute conductivity.

The region 1' of known conductivity might be given by the material that defines the border of an existing opening in a roof of the metallurgical vessel 1. Alternatively, a dedicated element of known conductivity may be arranged along the path of the sensor unit 4 to enable calibration into absolute conductivity.

It should also be realized that if the position of the material of known conductivity is known, this position may be used to calibrate the conductivity signal 40 into a vessel coordinate system, without the need for a position signal 42, provided that the lance 5 is displaced at a known and possibly fixed speed.

FIG. 5 also contains a graph that illustrates a spatial conductivity profile mapped to a vessel coordinate system. In the conductivity profile, dark dots indicate an alternative conductivity profile which is obtained by sampling only three conductivity values in the molten material (and a measurement value at the known conductivity, for calibration purposes). It should be realized that even such a low density profile may be useful for indicating the approximate location and extent of the matte layer M1, especially if the conductivity profile is given in absolute conductivity. Generally, it is be understood that a "signal profile" or "conductivity profile", as used herein, comprises at least two measurement values taken at different relative positions between the sensor unit 4 and the target material M, and normally at least 5 measurement values. In most practical situations, the measurement values are sampled at a rate of 1-100 Hz, which yields 30-3000 measurement values for a measurement session with a duration of 30 seconds.

Electrical conductivity is known to be dependent on temperature. In metals, electrical conductivity decreases with increasing temperature, whereas in semiconductors, electrical conductivity increases with increasing temperature. Over a limited temperature range, the electrical conductivity may be approximated as being directly proportional to temperature. To compare electrical conductivity measurements at different temperatures, they must be standardized to a common temperature. This dependence is often expressed as a slope in the conductivity-temperature graph, which may be written as:

$$\sigma_{T'} = \frac{\sigma_T}{1 + \alpha(T - T')}$$

where T is the measured absolute temperature, T' is the common temperature, $\sigma_{T'}$ is the electrical conductivity at the common temperature, $\sigma_T$ is the electrical conductivity at a measured temperature T, and $\alpha$ is the temperature compensation slope of the material.

Thus, if the temperature compensation slope $\alpha$ of the molten material is expected be significant within the range of temperatures observed in the vessel 1, or rather along the movement path of the sensor unit 4 during the measurement session, it may be desirable to install one or more temperature sensors, such as thermocouples, on the lance 5 e.g. in the vicinity of the sensor unit 4. The measurement system 10 may then obtain temperature data from the temperature sensors during the conductivity measurement, and correct the measurement values accordingly. Such correction may be applied to relative conductivity values, or be part of the calculation of absolute conductivity values.

Figure 6:
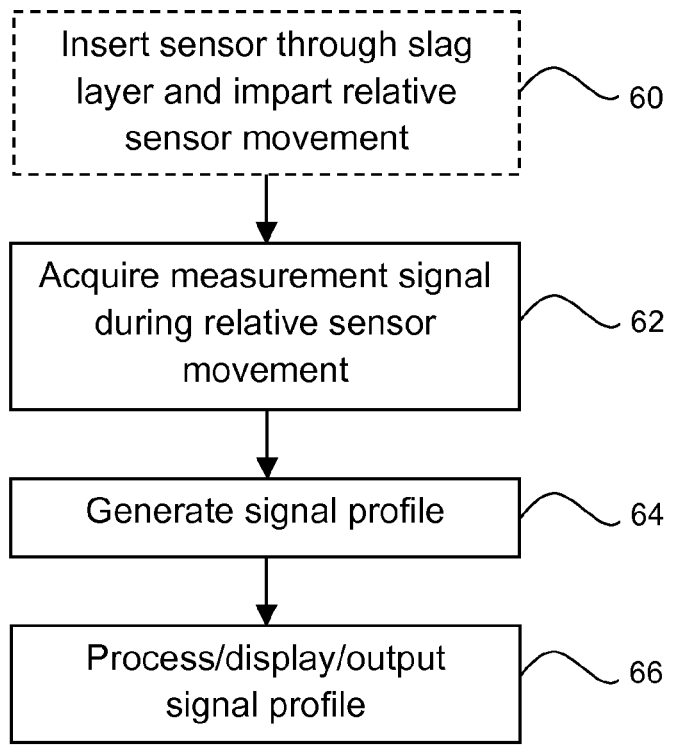
FIG. 6 is a flow chart of a method according to an embodiment of the invention.

FIG. 6 shows an example of a method a carried out during a measurement session for probing or investigating the target material M in the vessel. In step 60, the displacement unit 11 is activated to drive the lance 5 and the sensor unit 4 through the slag layer S and into the molten material, and then the relative movement is created by displacing the sensor unit 4 and/or the target material M (via tapping). In step 62, the measurement controller 13 is operated to acquire the measurement signal from the sensor unit 4 during the relative movement. In step 64, the signal processor 14 generates the conductivity profile. In the step 66, the signal processor 14 outputs the conductivity profile, or processes and/or displays the conductivity profile, e.g. for identification of the presence and/or location of different zones/layers S, M1, M2 in the target material M.

The movement of the sensor unit 4 and/or the molten material in step 60 may, but need not, be directly or indirectly controlled by the signal processor 14. However, by acquiring the above-mentioned position signal, or by the above-mentioned position calibration via one or more reference positions, the operation of the signal processor 14 and the measurement controller 13 may be executed independent of the displacement of the sensor unit 4 or the molten material. Thereby, the measurement system 10 may be fitted to a processing plant, without requiring any changes to any existing lance drive mechanism or tapping mechanism.

It is to be understood that the method in FIG. 6 may be used to investigate the target material M irrespective of the types of layers/zones. Thus, the probing method may give information about the slag layer S and/or any number of zones M1, M2 beneath the slag layer S. In the certain embodiments, e.g. as described in the foregoing, the probing method is primarily designed for obtaining a conductivity profile beneath the slag layer S in the target material M. However, the slag layer S need not be located at the top of the target material M. For example, in manufacturing of silica, the slag layer is formed at the bottom of the furnace/smelter used in the reduction process. In such an application, the probing method may thus be used to obtain a conductivity profile above the slag layer S in the target material M. The probing method may also be used for obtaining a conductivity profile in a target material without a slag layer.

It is to be understood that the functionality of the controller 13 and the signal processor 14 may be implemented by a single device. In all configurations, all or part of the functionality may be provided by dedicated hardware and/or by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/ means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The computing device may include one or more communication interfaces, such as a serial interface, a parallel interface, a USB interface, a wireless interface, a network adapter, etc, as well as one or more data acquisition devices, such as an A/D converter. The special-purpose software may be provided to the computing device on any suitable computer-readable medium, including a record medium, a read-only memory, or an electrical carrier signal.

The conductivity profile may be used in many different ways. In one embodiment, the conductivity profile is output for display on a screen, e.g. in the form of graph, possibly overlaid on a graphical illustration of the vessel. This will allow an operator to use the displayed conductivity profile as a basis for manual control and/or optimization of the metallurgical processing and/or tapping of material from the vessel. It is also conceivable that the operator is allowed to verify/input the location of one or more zones based on the displayed conductivity profile, whereby the signal processor calculates an amount of material in the vessel based on the identified zone(s). Returning to the example of copper processing, the amount of copper matte in the vessel may be calculated based on the extent of the matte layer given by the conductivity profile. Such calculations may also take into account any material build-up on the bottom of the vessel (as shown in FIG. 5). The extent of the build-up may be estimated based on the position signal, e.g. by comparing the position when the lance hits the apparent bottom of the vessel to a reference position obtained without any build-up.

In another embodiment, the conductivity profile is analyzed by automatic signal feature extraction techniques, with the purpose of identifying step-changes, plateaus, etc which are indicative of characteristics of the target material, such as the presence, location or extent of zones/layers, such as different material zones, mixing zones and layers within the target material. The output of such automatic analysis may be displayed for use in manual control of the metallurgical processing/tapping or it may be input to a system for automatic process/tapping control or automatic amount estimation.

Figure 7:
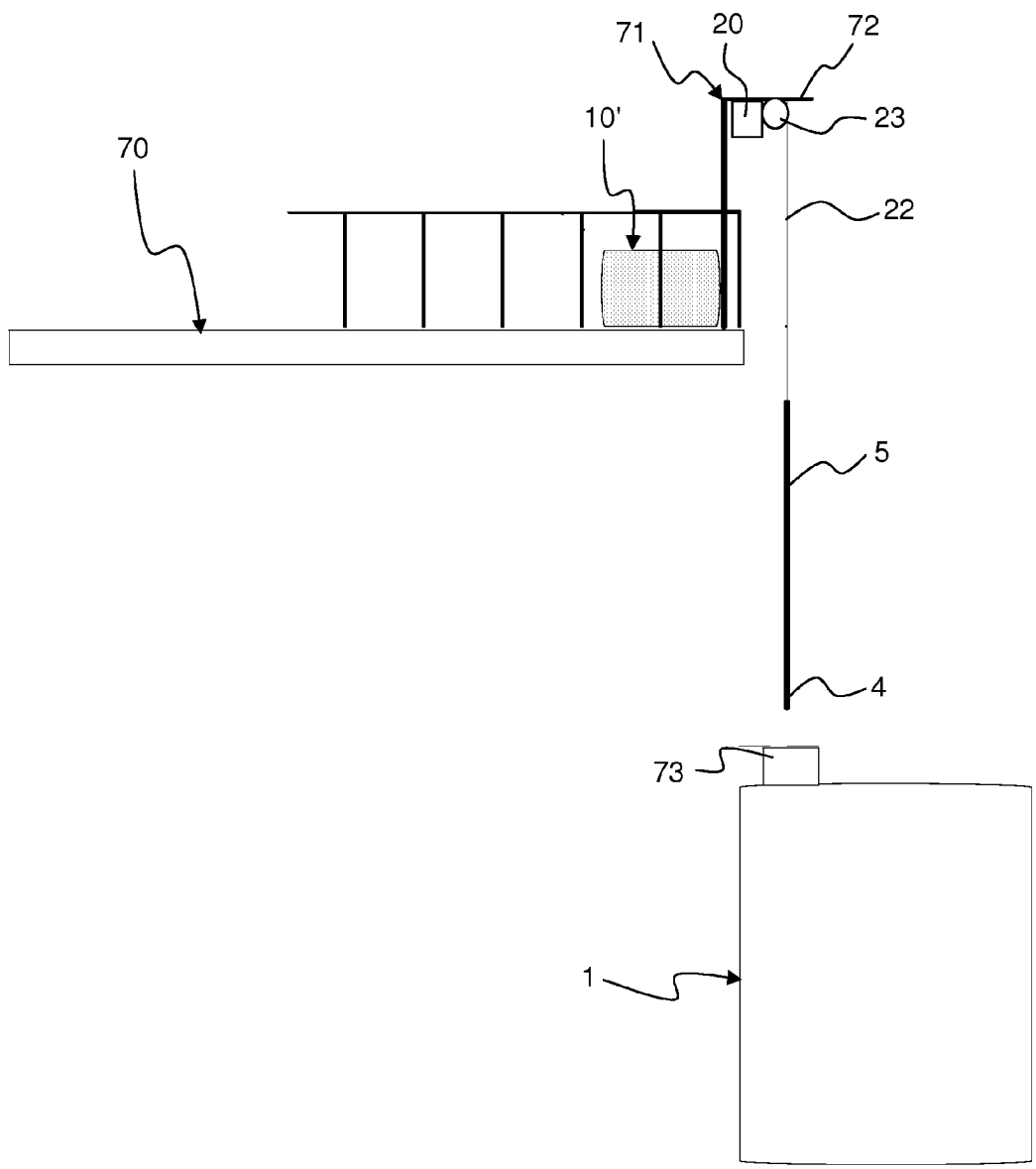
FIG. 7 is a side view of a measurement set-up in a processing plant.

FIG. 7 is a side view of an installation for conductivity profile generation in a plant for production of silica, and specifically in a slag holding furnace 1 used for cleaning slag obtained from a slag melting furnace. Electronic equipment 10' (e.g. the controller 13 and the signal processor 14) is arranged on a platform 70 above the furnace 1. Likewise, the winch 20 is arranged on a framework 71 fastened to the platform 70. The pulley 23 is fixed to a horizontal arm 72 of the framework 71 in a position directly above the flange 73 on the furnace roof. Thereby, the lance 5 is operable for movement in the vertical direction into and within the furnace 1. It should be understood that the detection of the conductivity profile is carried out under extreme and difficult conditions, e.g. high temperatures, heavy equipment and at significant heights. For example, the distance between the pulley 23 and the top of the furnace 1 is almost 7 meters in the illustrated installation.

Figure 8:
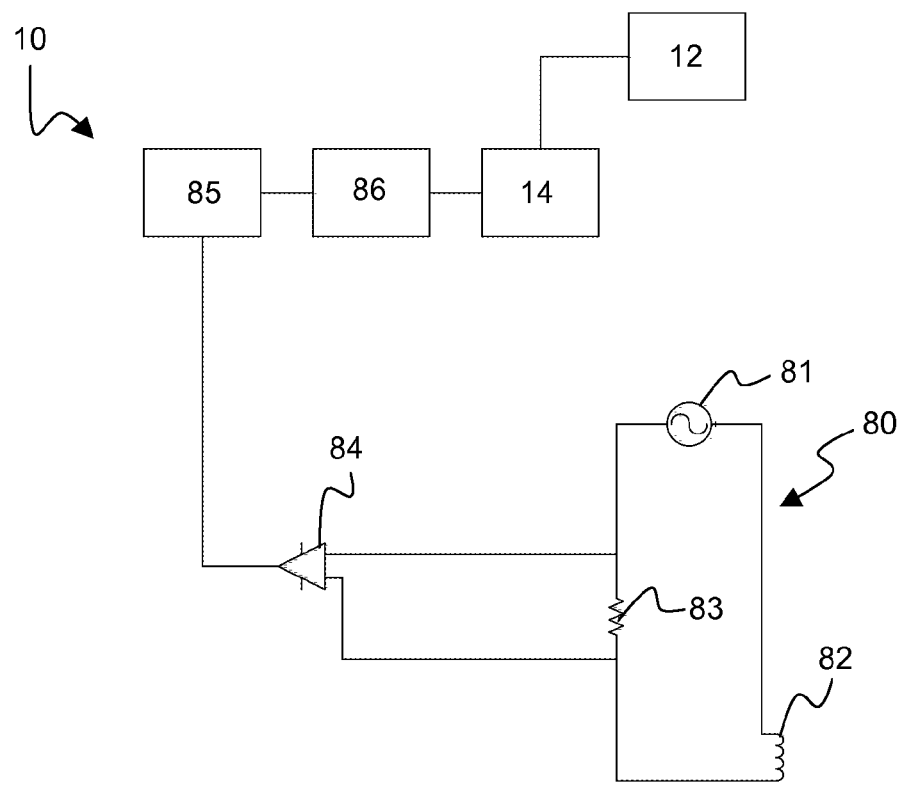
FIG. 8 is an electric diagram of a measurement system of transceiver configuration.
Figure 9:
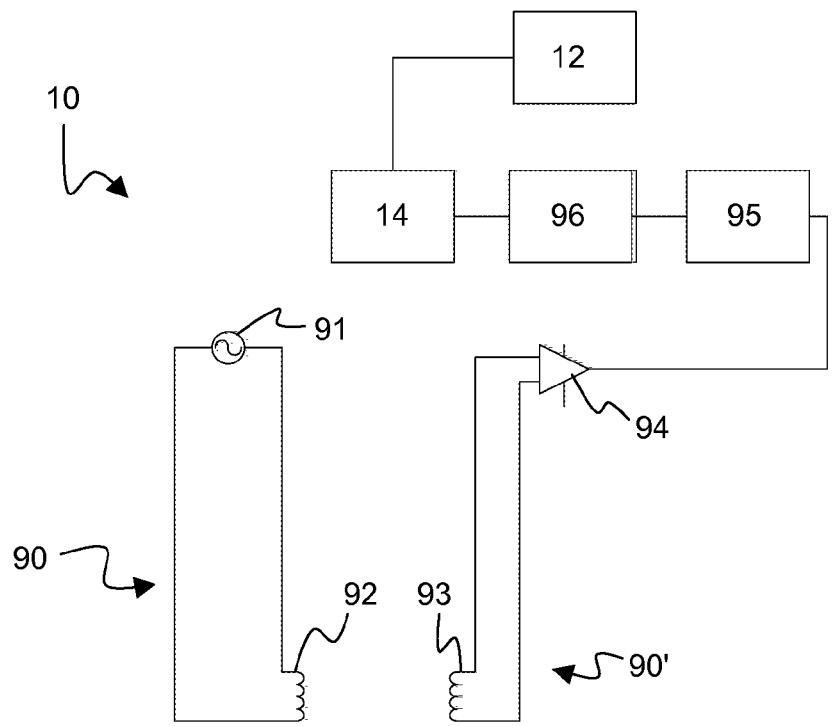
FIG. 9 is an electric diagram of a measurement system of transmitter-receiver configuration.
Figure 10:
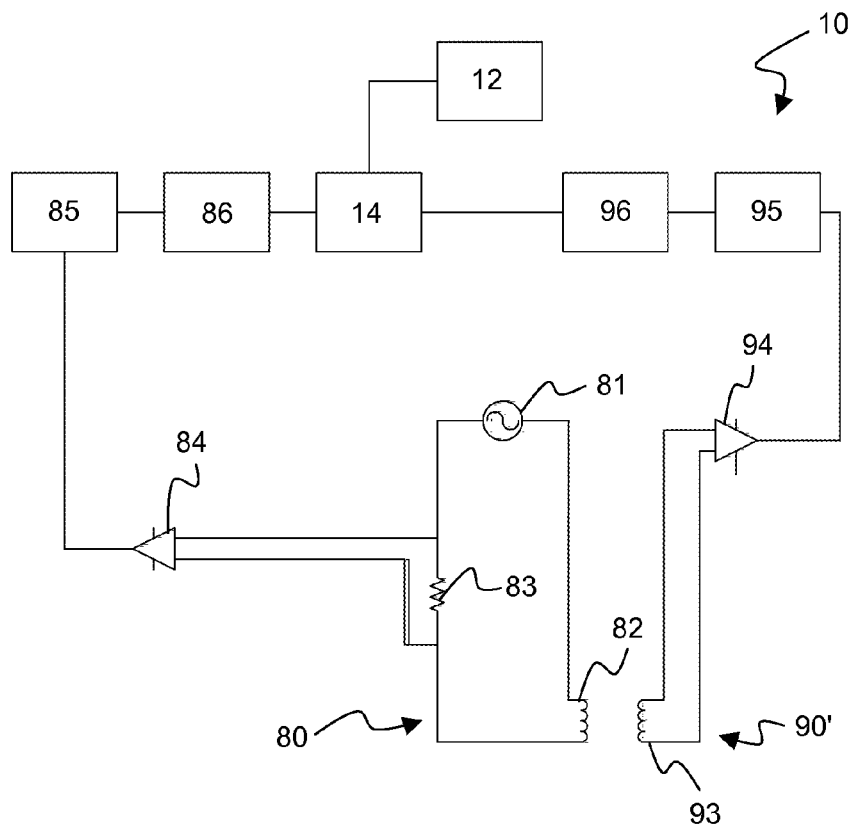
FIG. 10 is an electric diagram of a measurement system of transceiver-receiver configuration.

As indicated above, the sensor unit 4 operates by generating an electromagnetic field which extends into the surroundings of the sensor unit 4. Generally, the sensor unit 4 comprises one or more coils for generating the electromagnetic field. FIGS. 8-10 illustrate three different embodiments of the measurement system 10. It is to be understood that the sensor unit 4, which is physically installed on the lance 5, need only contain the coil(s), whereas all other components for generating the electromagnetic field and the measurement signal may be included in the controller 13 (FIG. 2) which is placed outside the vessel 1. For example, the coil(s) may be encased in a ceramic or other non-magnetic casing and then mounted at or near the front end of the lance with the wiring to the coil(s) passing back up through the lance (see dotted line in FIG. 2) so that a connection may be established to the controller 13. However, it is also conceivable that certain or all components of the controller 13 are included in the sensor unit 4.

FIG. 8 illustrates a measurement system 10 in which a single coil 82 is configured to act as a transceiver, i.e. it is used both for generating the electromagnetic field and for measuring changes in the thus-generated electromagnetic field.

In the example of FIG. 8, the measurement system 10 comprises a closed circuit ("transceiver coil circuit") 80 with a voltage source 81 for generating a fixed AC voltage at a given frequency, and the coil 82 connected in series with a precision resistor 83. A differential amplifier 84 has its inputs connected to terminals on either side of the resistor 83. The output of the differential amplifier 84 is connected to an input of an analog-to-digital converter (ADC) 85. The output of the ADC 85 is connected to the input of a digital filter 86, which is configured to isolate a measurement signal at the given frequency of the voltage source 81. The output of the digital filter 86 is connected to the signal processor 14 which samples and processes the measurement signal for generation of the conductivity profile. The signal processor 14 is also connected to the position-sensing unit 12 to sample and process a position signal. As described below, the measurement signal is essentially generated as a measure of the impedance in the transceiver coil circuit 80. In the following, the measurement signal obtained in the transceiver coil circuit is denoted a "T-signal".

During operation of the measurement system 10, the voltage source 81 is set to generate the fixed AC voltage, which thus forces an electrical current through the coil 82 and the precision resistor 83. The current flowing through the coil 82 generates an electromagnetic field around the coil 82. The conductivity of the surrounding material influences the electromagnetic field and thus the inductance of the coil 82. When the impedance (inductance) of the coil 82 changes, so does the magnitude of the electrical current that flows through the coil 82. It is realized that the potential difference over the precision resistor 83 is representative of the magnitude of the electrical current, and thus the conductivity of the surrounding material. The potential difference is amplified by the differential amplifier 84, digitized by the ADC 85, filtered by the digital filter 86 and provided as the measurement signal (T-signal) to the signal processor 14. The magnitude of the T-signal (peak voltage, peak-to-peak voltage, RMS voltage, etc) is thus representative of the conductivity of the surrounding material. An example of the T-signal is shown as the conductivity signal 40 in FIG. 4.

It is realized that the coil 82 acts as both a transmitter and receiver. The coil 82 is therefore referred to as a "transceiver coil" in the following, although it may also be denoted a transmitter coil.

FIG. 9 illustrates a measurement system 10 which includes a transmitter coil 92 operable to generate the electromagnetic field, and a separate receiver coil 93 operable to sense the electromagnetic field and any changes thereto. Like the coil 82 in FIG. 8, the transmitter coil 92 is included in a closed circuit ("transmitter coil circuit") 90 and connected to a voltage source 91 that generates a fixed AC voltage at a given frequency, thereby causing the coil 92 to generate the electromagnetic field. The receiver coil 93 is located within the range of the electromagnetic field, which thereby induces an electrical current in a receiver coil circuit 90'. The electrical current causes a potential difference between the terminals of the receiver coil 93. This potential difference is representative of the conductivity of the medium surrounding the transmitter and receiver coils 92, 93. The potential difference is amplified by a differential amplifier 94, digitized by an ADC 95, filtered by a digital filter 96 and provided as a measurement signal to the signal processor 14. Like in FIG. 8, the magnitude of the measurement signal is representative of the conductivity of the surrounding material. In the embodiment of FIG. 9, however, the measurement signal is essentially generated as a measure of the mutual inductance between the transmitter coil 92 and receiver coil 93. In the following, the measurement signal obtained in the receiver coil circuit is denoted an "R-signal".

It has been found that the R-signal, compared to the T-signal, is more sensitive to changes in the surrounding conductivity. It is currently believed that the T-signal is mostly representing changes in the strength or magnitude of the generated electromagnetic field, whereas the R-signal also represents changes in the extent or shape of the generated electromagnetic field. As the sensor unit 4 is moved relative to the target material, and passes regions of different conductivity, the shape of the generated electromagnetic field is likely to change, causing corresponding changes in the R-signal.

FIG. 10 illustrates a measurement system 10 which is a combination of the systems in FIGS. 8 and 9. Thus, the signal processor 14 receives a first measurement signal (T-signal) indicative of the electrical current flowing through a transceiver coil circuit 80 and a second measurement signal (R-signal) indicative of the electrical current flowing through a receiver coil circuit 90'. As explained in relation to FIG. 8, the electrical current flowing through the transceiver coil circuit 80 is affected by the surroundings of the transceiver coil 82. This change will be detected by the receiver coil circuit 90'. However, the receiver coil circuit 90' will also detect changes in the mutual inductance between the transceiver coil 82 and receiver coil 93. By providing both the first and second measurement signals to the signal processor 14, the signal processor 14 is able to discriminate between these effects to provide a more precise and/or more robust representation of the conductivity of the surrounding material.

Figure 11:
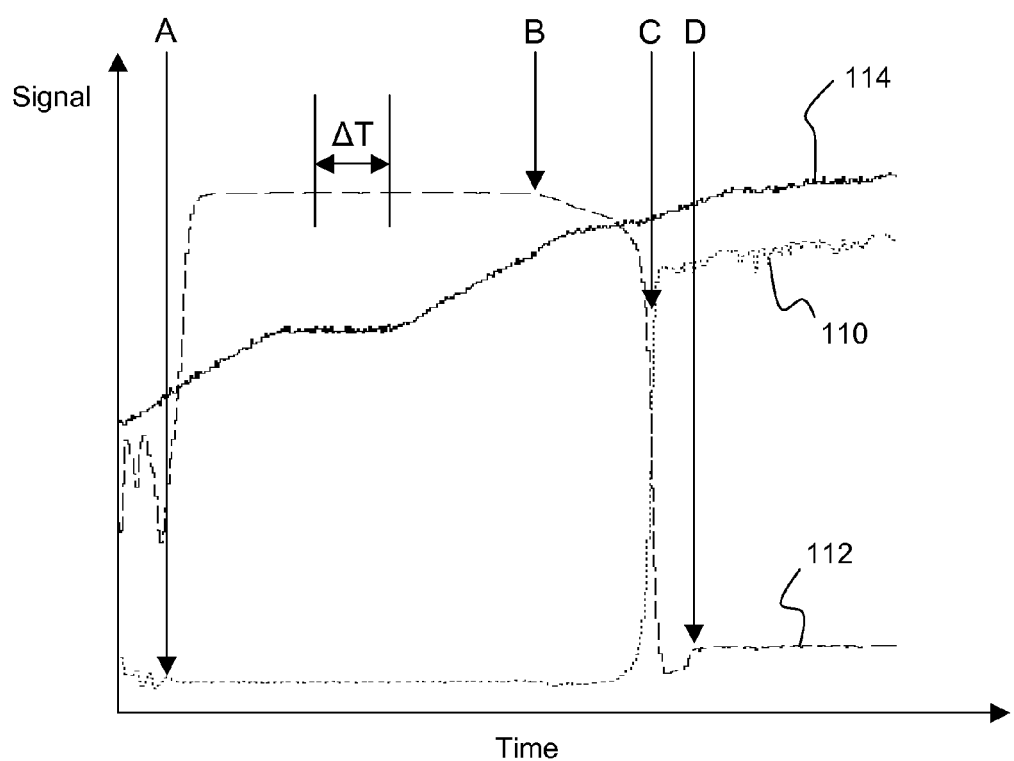
FIG. 11 is a graph of measurement signals obtained in the measurement system of FIG. 10.

FIG. 11 is a plot of a T-signal 110, an R-signal 112, and a position signal 114 obtained as a function of time while the lance 5 (and sensor unit 4) is lowered into a metallurgical vessel. The position signal 114 represents distance from a starting position above the vessel. It should be noted that the T-signal 110, which has been autoscaled relative to the R-signal 112, is at least one order of magnitude weaker than the R-signal. The signals 110, 112 are raw signals which have not be processed to represent conductivity, as seen by the fact that the T-signal 110 increases while the R-signal 112 decreases. Nevertheless, the temporal behavior of each signal 110, 112 reflects changes in surrounding conductivity. Arrow A indicates the time when the sensor unit 4 passes through the vessel roof, which may be detected in both signals 110, 112. Arrow B indicates the time when the sensor unit reaches the slag layer (S in FIG. 1), which may be detected by the onset of a gradual decrease in the R-signal 112. It may also be detected as a small change in the T-signal 110. In the illustrated example, arrow B is set at the time when the R-signal reaches 99% of a baseline, which is obtained by averaging the R-signal over a time period AT when the sensor unit is in the vessel above the target material. In a variant, arrow B may be set at the time when the T-signal reaches 100.05% of a corresponding baseline obtained by averaging the T-signal over the time period AT. Arrow C indicates the time when the sensor unit first reaches the matte layer (M1 in FIG. 1), represented by a steep change in the signals 110, 112. In the illustrated example, arrow C is set at the time when the R-signal reaches 50% of the above-mentioned baseline. In a variant, arrow C may be set at the time when the T-signal 110 reaches 102% of the relevant baseline. Arrow D indicates when the coils of the sensor unit are fully submerged in the matte layer, which may be detected as a leveling in the signals 110, 112, and in particular by the end of an undershoot in the R-signal 112. Although not indicated in FIG. 11, a mixing zone (M2 in FIG. 1) may be detected in the R-signal and/or T-signal between the arrows B and C.

It should be realized that the availability of both the T-signal 110 and the R-signal 112 may make it possible for the signal processor 14, e.g. based on automatic signal feature extraction, or the operator by visual inspection of the signals, to correlate signal features occurring in both signals 110, 112 in order to improve the analysis of the target material, e.g. to identify the locations of interfaces or to derive an absolute or relative conductivity profile. It may also be possible to extract supplementary information from the curves 110, 112, i.e. information relating to different characteristics of the vessel and/or the target material.

Furthermore, depending on the relative placement of the transceiver and receiver coils 82, 93, the signal processor 14 or the operator may be able to determine the approximate location of a local change in conductivity, which may e.g. be used to detect and/or provide a measure of the burn-off of the above-mentioned protective sleeve during the measurement session, and/or to be used in the generation of the conductivity profile.

It has thus been found that the use of a receiver coil circuit 90', as exemplified in FIGS. 9 and 10, may serve to improve the conductivity measurements. On the other hand, it has been found that the embodiment in FIG. 8 with a transceiver coil circuit only, may exhibit an improved insensitivity to electrical/electromagnetic disturbances compared to the embodiments in FIGS. 9 and 10. Such disturbances may e.g. be generated by electrical heating elements in an electric smelter/furnace.

The skilled person realizes that the fixed voltage source 81, 91 in the measurement systems 10 of FIGS. 8-10 may be replaced by a fixed current source, and that the digital filters 86, 96 may be replaced by analog filters.

In a variant (not shown), the signal processor 14 receives measurement signals that indicate the electrical current in the transceiver/transmitter coil circuit 80, 90 and the voltage across the transceiver/transmitter coil 82, 92. Based on these measurement signals, the signal processor 14 may calculate the phase difference between voltage and current in the transceiver/transmitter coil circuit 80, 90. This phase difference will change when the conductivity changes in the surroundings of the coil 82, 92, and the signal processor 14 may use the phase difference to determine the conductivity in the surrounding material. It is also conceivable to combine such a phase difference measurement with the impedance measurement in the transmitter/transceiver coil circuit 80, 90 (FIGS. 8 and 10) and/or the measurement of the mutual inductance (FIGS. 9 and 10) to further improve the conductivity measurement.

Figure 12:
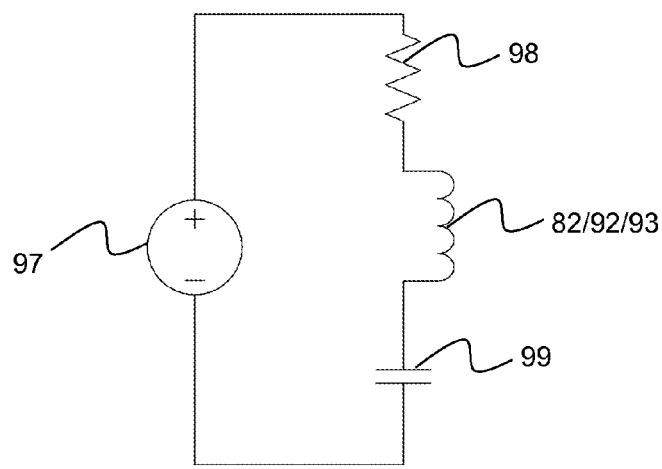
FIG. 12 is a electric diagram of an RLC circuit for signal detection in one embodiment.

In another variant (not shown), the transmitter/transceiver coil 82, 92 and/or the receiver coil 93 is connected in a resonant circuit, such as an RLC circuit as shown in FIG. 12. An RLC circuit comprises a power source 97, a resistance R (represented by a resistor 98), a capacitance C (represented by a capacitor 98), and an inductance L (including the coil 82, 92, 93), which are connected in series (as shown) or in parallel. The resonance frequency $f_0$ of the RLC circuit is given by $$f_0 = \frac{1}{2\pi\sqrt{LC}}$$

The inductance L of the coil 82, 92, 93 will change with the conductivity of the surrounding material, and thus the conductivity may be determined by measuring the resonance frequency $f_0$. Circuitry for measuring the resonance frequency in RLC circuits are commercially available.

In all of the above embodiments, variants and alternatives the resolution of the measured conductivity may be optimized by adjusting the frequency of the transmitter/transceiver coil 82, 92 (i.e. the frequency of the AC voltage/current driving the generation of the electromagnetic field) to a particular vessel 1 and the target material M therein. Embodiments of the invention may operate at frequencies in the range of about 1-1000 kHz, and typically in the range of about 1-100 kHz. It is also conceivable to design the measurement system 10 to operate at more than one frequency, e.g. by installing plural transmitter/transceiver coil circuits 80, 90 on the lance 5 to operate at a respective frequency, whereby the signal processor 14 is connected to receive measurement signals obtained at the different frequencies. This may serve to improve the quality of the conductivity profile.

Furthermore, even if the above description refers to single coils, it is to be understood that the transmitter/transceiver/receiver coil 82, 92, 93 may be formed as a combination of individual sub-coils.

Still further, the strength of the generated magnetic field may need to be adapted to the measurement situation. This may be accomplished by adapting one or more of the number of turns of wire in the coil 82, 92, 93, the amount of current flowing in the coil 82, 92, 93, the ratio of the coil length to the coil width, and the type of material in the core of the coil 82, 92, 93. This is merely a matter of routine experimentation for the person skilled in the art.

Figures 13A, 13B, 13C:
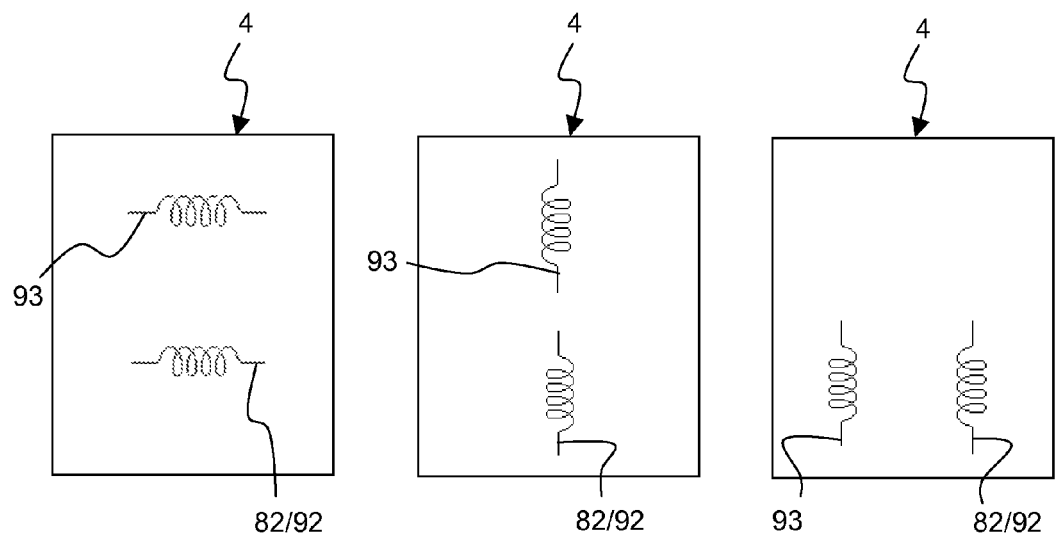
FIGS. 13A-13C indicate different coil arrangements in the measurement systems of FIGS. 9 and 10.

Likewise, the configuration and mutual placement of the transmitter/transceiver coil 82, 92 and the receiver coil 93 may be optimized for a given measurement situation. FIGS. 13A-13C illustrate three alternative arrangements of the transmitter/transceiver coil 82, 92 and the receiver coil 93 in the sensor unit 4. Other arrangements are possible, e.g. switching the positions of coil 82, 92 and coil 93, or arranging one coil vertically and the other horizontally. Still further, the spacing of coil 82, 92 and coil 93 may be adapted to achieve a desired sensitivity, or other property, of the R-signal.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, the measurement signal or the signal profile may represent any other entity equivalent to the conductivity, such as resistivity.

Further, it is possible to use more than one sensor unit, which may be arranged on one or plural lances, or on sub-lances on a common lance. With reference to the embodiments in FIGS. 9 and 10, it is likewise possible to arrange the receiver coil 93 on a different lance/sub-lance than the transceiver/transmitter coil 82, 92.

It is also to be realized that the spatial conductivity profile does not have to be mapped to positions, but may be given as a function of time (cf. conductivity signal 40). Such a conductivity profile may be inspected/processed for identification of zones by itself or with reference to a separate position signal (cf. position signal 42 in FIG. 4).

Still further, the measurement signal need not be sampled at discrete time points, but may instead be obtained as an analog signal, i.e. continuously.

Instead of slag (or in addition to slag), the top layer S may contain some form of raw or pre-refined material. It is also realized that the molten material beneath the top material layer S may contain non-melted fractions, and gaseous substances. In fact, it is possible to apply the inventive solution for enabling identification of zones in non-melted target material, such as powders or granulates. Irrespective of target material, the zones may be defined by at least one of: a unique composition of matter, a unique degree of melting, and unique degree of mixing. It is also possible that certain zones have essentially the same conductivity (or change in conductivity along the measurement path). Such zones may be identified/discriminated in the conductivity profile based on their location in relation to other zones/layers with different conductivity (or change in conductivity), e.g. based on an expected ordering of zones in the target material.

The invention claimed is:

1. A method of probing an electrically conductive target material in a metallurgical vessel, said method comprising the steps of:
    immersing a sensor in the target material;
    moving the sensor on a movement path in at least one direction in the target material, the movement path extending through at least one molten metal or semiconductor material;
    acquiring a measurement signal from the sensor while the sensor is moving on the movement path in the target material, the measurement signal being indicative of electrical conductivity in the vicinity of the sensor; and
    generating, based on the measurement signal, a signal profile indicative of the electrical conductivity as a function of the sensor movement,
    wherein the method further comprises the steps of operating at least one coil in the sensor to generate an electromagnetic field around the sensor, and generating the measurement signal to represent momentary changes in the electromagnetic field.

2. The method of claim 1, wherein the step of generating the electromagnetic field comprises operating a drive circuit comprising a transmitter coil and a supply of an alternating source signal for the transmitter coil.

3. The method of claim 2, wherein the step of generating the measurement signal comprises sensing the impedance in the drive circuit.

4. The method of claim 3, wherein the step of sensing the impedance in the drive circuit comprises sensing a potential difference over a resistor means connected in series with the transmitter coil.

5. The method of claim 3, wherein the step of sensing the impedance in the drive circuit comprises sensing a resonance frequency of a resonance circuit including the transmitter coil.

6. The method of claim 3 wherein the step of generating the measurement signal comprises sensing the mutual inductance between the transmitter coil and a receiver coil spaced from the transmitter coil and wherein the step of generating the signal profile comprises generating a first signal profile based on a first measurement signal representing the impedance in the drive circuit and a second signal profile based on a second measurement signal representing the mutual inductance.

7. The method of claim 6, further comprising identifying one or more characteristics of the target material based on a combination of the first and second signal profiles.

8. The method of claim 2, wherein the step of generating the measurement signal comprises sensing the mutual inductance between the transmitter coil and a receiver coil spaced from the transmitter coil.

9. The method of claim 8, wherein the step of sensing the mutual inductance comprises sensing a potential difference over the receiver coil.

10. The method of claim 8, wherein the step of sensing the mutual inductance comprises sensing the resonance frequency of a resonance circuit including the receiver coil.

11. The method of claim 2, wherein the step of generating the measurement signal comprises sensing a phase difference between the voltage over the transmitter coil and the induced current through the transmitter coil.

12. The method of claim 1, wherein the sensor is moved along the movement path in at least two passages, and wherein the measurement signal is acquired by combining measurement values obtained during different passages of the movement path.

13. The method of claim 1, further comprising the step of acquiring a position signal indicative of the location of the sensor while the sensor is translated on the movement path, wherein the signal profile is generated based on the measurement signal and the position signal to be indicative of the electrical conductivity as a function of the location of the sensor.

14. The method of claim 13, wherein the step of generating the signal profile comprises matching time points in the measurement signal to time points in the position signal.

15. The method of claim 1, further comprising the step of performing automatic feature extraction on the signal profile to identify one or more characteristics of the target material.

16. A non-transitory computer-readable medium comprising program instructions that, when executed by a processor, performs the method of claim 1.

17. A computer program product loadable into a non-transitory memory of a computing device for performing the method of claim 1.

18. The method of claim 1, further comprising maintaining no galvanic contact between the sensor and the target material during the step of moving the sensor on a movement path in at least one direction in the target material.

19. A device for probing an electrically conductive target material in a metallurgical vessel, said device comprising:
  a sensor configured to be immersed in the target material and moved on a movement path in at least one direction in the target material, the movement path extending through at least one molten metal or semiconductor material;
  a controller configured to acquire a measurement signal from the sensor while the sensor is moving on the movement path in the target material, the measurement signal being indicative of electrical conductivity in the vicinity of the sensor; and
  a signal processor configured to generate, based on the measurement signal, a signal profile indicative of the electrical conductivity as a function of the sensor movement;
  wherein the controller is further configured to operate at least one coil in the sensor to generate an electromagnetic field around the sensor, and to generate the measurement signal to represent momentary changes in the electromagnetic field.

20. The device of claim 19, further comprising a position sensor configured to generate a position signal indicative of the location of the sensor while the sensor is translated on the movement path in the target material, wherein the signal processor is configured to generate, based on the measurement signal and the position signal, the signal profile to be indicative of the electrical conductivity as a function of the location of the sensor.

21. The device of claim 19, wherein a plant for processing of an electrically conductive target material, comprises:
  a metallurgical vessel configured to contain the target material;
  a lance;
  the sensor attached to the lance and configured to sense electrical conductivity;
  a drive mechanism mechanically connected to the lance and configured to move the lance with respect to the target material; and
  the device.

22. A method of probing an electrically conductive molten target material in a metallurgical vessel, the molten target material including at least one metal or semiconductor material, said method comprising the steps of:
  immersing a sensor in the molten target material;
  tapping the molten target material from the metallurgical vessel while the sensor is held in a fixed position within the metallurgical vessel;
  acquiring a measurement signal from the sensor while the molten target material moves passed the sensor, the measurement signal being indicative of electrical conductivity in the vicinity of the sensor; and
  generating, based on the measurement signal, a signal profile indicative of the electrical conductivity as a function of the molten target material movement,
  wherein the method further comprises the steps of operating at least one coil in the sensor to generate an electromagnetic field around the sensor, and generating the measurement signal to represent momentary changes in the electromagnetic field.

* * * * *